United States Patent [19]

Gaines et al.

[11] 3,960,632
[45] June 1, 1976

[54] METHOD OF PREPARING A DISPENSING PAD FOR FINGERPRINTING REAGENTS

[75] Inventors: Jerome Gaines, Van Nuys; Herbert M. Conrad, Santa Monica, both of Calif.

[73] Assignee: Veriprint Systems Corporation, Chatsworth, Calif.

[22] Filed: Sept. 26, 1974

[21] Appl. No.: 509,326

[52] U.S. Cl. .............................. 156/245; 118/31.5; 118/264; 427/1; 428/281
[51] Int. Cl.² ............................................ B29C 5/00
[58] Field of Search ............. 156/145, 242, 245, 39; 117/.5, 1, 1.7; 118/31.5, 264, 269, 270; 264/86, 222; 101/125, 333

[56] References Cited
UNITED STATES PATENTS

| | | | |
|---|---|---|---|
| 603,841 | 5/1898 | Fairbank et al. | 118/264 |
| 637,985 | 11/1899 | Adams | 118/264 |
| 714,512 | 11/1902 | Nicholas | 118/264 |
| 721,474 | 2/1903 | Smith | 118/264 |
| 1,241,322 | 9/1917 | Woody | 118/264 |
| 2,206,042 | 7/1940 | Novae | 156/39 |
| 2,723,476 | 11/1955 | Lyon | 118/264 |
| 3,851,619 | 12/1974 | Cofield et al. | 118/31.5 |

*Primary Examiner*—Caleb Weston
*Attorney, Agent, or Firm*—Robert Louis Finkel

[57] ABSTRACT

An inkless fingerprinting system comprises a porous, non-yielding reagent pad saturated with a substantially colorless metallic salt solution, preferably based on ferric chloride, and means for applying an organic developer, preferably 8-hydroxyquinoline, to a latent fingerprint obtained by pressing the distal surface of a finger against the reagent pad and transferring the reagent adhering to the ridges of the finger onto a paper or plastic surface. The reagent and the developer interact to form a colored chelate and, thereby, render the fingerprint visible.

10 Claims, 8 Drawing Figures

METHOD OF PREPARING A DISPENSING PAD FOR FINGERPRINTING REAGENTS

BACKGROUND AND SUMMARY OF THE INVENTION

This invention relates to systems for transferring fingerprints and, more particularly, to such systems which utilize an image transfer medium which does not stain the subject's finger with a colored ink.

The art of "taking" fingerprints and comparing the images so obtained with pre-recorded ones to establish the identity of the person fingerprinted is old.

The procedure normally used requires that the subject's finger be first pressed against a smooth plate, usually of glass, on which a thin layer of ink has been deposited with the aid of a brayer, and then rolled against a piece of paper or other ink-printable medium. The process is time consumming and messy, and requires considerable skill on the part of the practitioner, especially in the techniques of spreading the ink on the plate, applying the finger to the inked surface, and transferring the print to the receiving surface. For these reasons the practice is generally restricted to the criminal investigation, security and administrative identification fields.

Modern commerce, with its increasing reliance on negotiable documents such as checks, bank drafts and the like, and on credit transactions using credit cards, for its smooth operation is in great need of a simple and foolproof method of establishing the identity of individuals presenting themselves as the rightful owners of such documents and demanding that they be honored without delay. The best method of proving, or disapproving, identity in the event of a subsequent dispute as to the right of the claimant to the funds, goods or services supplied, would be to retain a clear fingerprint of the individual, a thumbprint for example, as part of the receipt, endorsement, or other memorandum of the transaction.

That such an identification system is not in common use can be directly attributed to the inconvenience of prior art methods of securing fingerprints. Customers, rightly, object to ink-smeared fingers, time delays, and other disturbing aspects of these methods.

Many proposals to simplify the procedures or to avoid the problems complained of have been made. These range from methods employing the natural secretions of the skin to produce a latent image which can be developed with chemical reagents sensitive to the amino acids or other constitutents transferred to a receiving surface, to complex automated electro-optical devices which reproduce "live" prints photographically. Most such proposals contain features which are as undesirable, for successful commercial use, as those involved in the conventional fingerprinting process. Consequently, none of these has achieved any considerable success in the marketplace.

It is the primary object of the subject invention to teach a simple, convenient, economical process for permanently recording fingerprints.

It is a further object of the invention to teach the use of non-staining chemical compositions, and developers for them, which permit the formation of highly visible sharply defined fingerprint images on a variety of substrates.

It is another object of the invention to teach the construction, method of production, and use of hard-surfaced nonsmearing pads for the storage and application of such non-staining chemical compositions.

It is yet another object of the invention to teach the construction and use of a compact self-contained portable kit with which the aforementioned process may be performed anywhere by minimally trained personnel.

The subject invention attains these and other objects by providing a hard-surfaced pad with controlled internal porosity and impregnated with a soluble metallic salt, preferably anhydrous ferric chloride, dispersed in a glycerine carrier medium. Applying the distal surface of the subject's finger against the unyielding surface of the pad transfers a thin, uniform layer of the metallic salt to the ridges of the skin. The salt is deposited on a suitable substrate by pressing the finger against it with a rolling motion.

A developer in the form of an organic base, preferably 8-hydroxyquinoline dissolved in acetone, is applied to the latent print on the substrate as a fine spray from an aerosol container. The metallic salt and the organic base form a colored chelate and render the fingerprint visible and permanent.

In kit form the invention comprises a box with a hinged cover and an inset top. A resilient metal plate attached to the underside of the cover is adapted to receive and hold a document or instrument to be identified with the subject's fingerprint. An opening in this plate is in registry with a similar opening in the top. The aforementioned pad, impregnated with the fingerprinting medium, is recessed in the top of the box.

An aerosol container, charged with developer, is securely mounted in the box below the top, with its spray orifice directed to discharge a metered quantity of spray against that portion of the document exposed through the openings in the cover and the top, when the cover is closed against the box. A finger-operated, spring-biased lever arm is mounted through one side of the box to allow the operator to actuate the aerosol valve.

In operation, the document or instrument is placed under the resilient plate and aligned to expose the intended location of the fingerprint in the opening. The subject's finger is rolled lightly over the pad and then applied to the exposed surface of the document. A handle mounted on the outside of the cover supports it during this process.

The cover is then closed and the valve-lever actuated, thereby discharging a metered quantity of developer against the invisible image on the document, rendering it visible and permanent and providing positive identification of the subject on the document or instrument.

The principal features of the invention will be described in detail below, with reference to the preferred embodiment thereof, as illustrated in the accompanying drawings.

DESCRIPTION OF THE PREFERRED EMBODIMENTS

Figure 1:
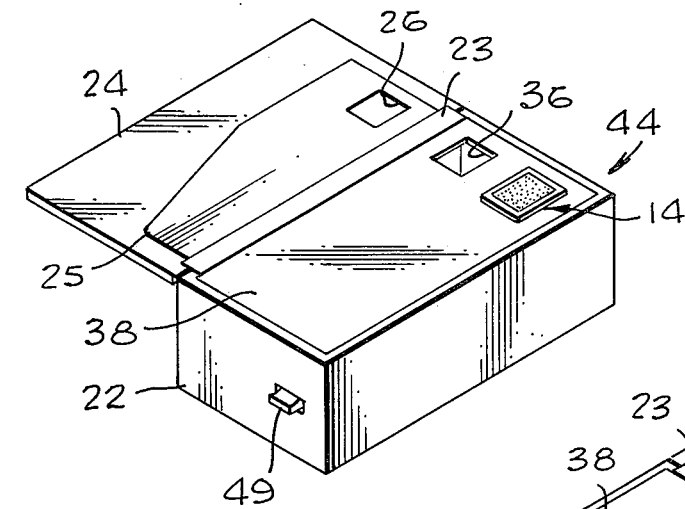
FIG. 1 is a perspective view of the fingerprinting device of the invention.

A fingerprinting device 44 is shown in the perspective view of FIG. 1, encased in a box 22 with a hinged cover 24. The box may be made of light but sturdy construction and adapted to be carried about for use at any convenient location, or may be built into a permanent structure, such as a bank teller's window or supermarket cashier's stand. A planar top 38 is inset into the upper periphery of the box 22 and is provided with an opening 36 and an adjacent cutout in which a pad assembly 14 is recessed. A resilient retainer 25 overlays the inner surface of the cover 24 and is affixed thereto along its edge proximate to hinge 23 interconnecting the cover with the box 22. An opening 26 in the retainer 25 is similar in size and shape to the opening 36 in the top 38 and is located to coincide therewith when the cover is closed against the box.

Figure 2:
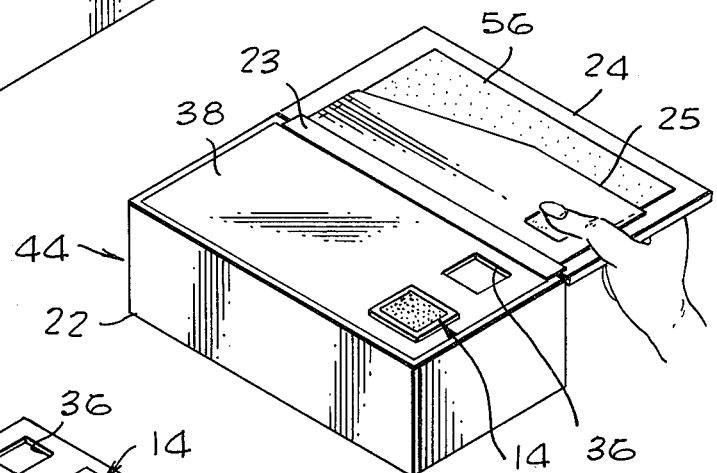
FIG. 2 is another perspective view of the fingerprinting device, showing a thumbprint being transferred to a document therein.

The interrelation of the several parts of the device will become clear from a brief explanation of the use thereof, and with particular reference to the perspective view of FIG. 2.

Upon the presentation of a typical document such as check 56, the operator of the fingerprinting device opens the cover 24, thereby exposing the retainer 25 and the top 38, and slides the document 56 into the space between the retainer and the cover. The operator then aligns the document 56 so that a suitable, preferably unobstructed, area thereon is in register with the opening 26.

A handle 29 is attached to the outside of the cover 24 and serves a dual purpose. It provides a ready handhold to the operator for opening and closing the fingerprinting device, and it also provides structural support to the cover during the imprint of the latent image on the document 56.

The subject whose identity is to be established on the document 56 is next asked to roll his thumb lightly over the surface of pad 14 and then to press the wetted skin surface against the area of the document exposed through opening 26, as shown in FIG. 2.

The pad 14 has a hard, but finely porous, surface and the matrix below the surface is saturated with a substantially colorless liquid solution or dispersion of a metallic salt. Rolling the subject's fingers lightly over the pad 14 transfers a thin layer of this liquid onto the ridges of the skin; the subsequent pressing of the finger against the surface of the document 56 transfers an image of the ridge pattern to that surface.

The image on the document is developed by spraying a developing agent in the form of an organic base on the latent image. This is accomplished by closing the cover 24 against the box 22, with the document 56 still secured firmly under the retainer 25. This brings the opening 26, framing the latent fingerprint into register with the opening 36 in the top 38. The developing agent is held in an atomizing spray can, preferably an aerosol dispenser 42, located below the top 38. In the aerosol dispenser form pressure is exerted on the fluid contents by a suitable chemically inert propellant in such a manner that actuating a valve 45 on the container 42 releases a pre-determined amount of the liquid developer. The orifice of the valve 45 is so aimed that the spray exits through the opening 36 and covers the area of the latent image in register therewith.

Figure 3:
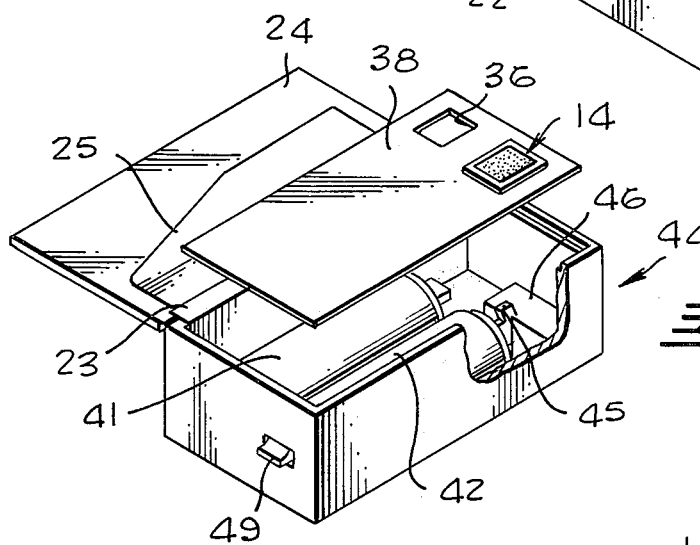
FIG. 3 is a perspective, partly exploded, view of the device of FIG. 1, showing the arrangement of the developer supply system.
Figure 4:
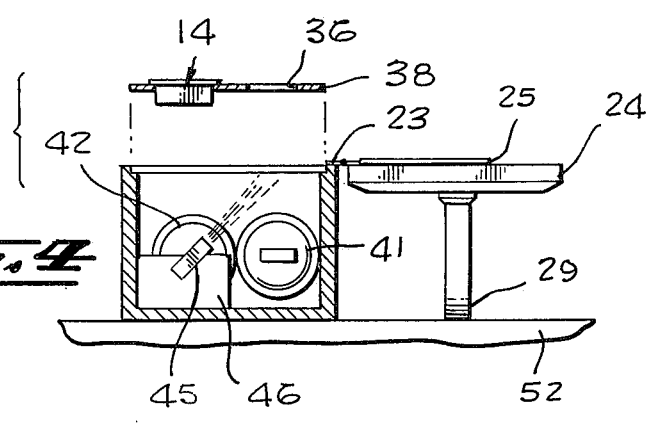
FIG. 4 is a transverse section, taken along section line 4—4 of FIG. 3, of the fingerprinting device.

As shown in FIG. 3, and in the transverse section of FIG. 4, the aiming and location of the valve 45 are determined by a mating slot milled into a block 46; the relative motion for developer discharge is attained by a simple lever system operated by external knob 49 thrusting the container 42 towards the block 46. With this arrangement, to develop the latent print the operator merely closes the cover 24 and depresses the knob 49.

Almost immediately on contact the organic base of the developer solution forms a deeply colored chelate wherever the document 56 has been impressed with the latent print. The chelate formed by the interaction of ferric chloride and 8-hydroxyquinoline is a dark black highly stable composition which adheres tenaciously to paper, plastics and a wide variety of other materials. We have found it to be ideal for producing permanent, sharply defined prints suitable for comparison with other fingerprints by conventional or automated techniques.

The entire fingerprinting process, opening the cover, inserting the document into the retainer, wetting the finger, transferring the print, closing the cover, actuating the developer valve, and removing the printed document, can be performed in a few moments, even by an operator with little special skill. The small amount of fingerprinting medium remaining on the subject's finger or thumb is neither visible nor irritating. Experience has shown that it wears off in normal daily activities in a few minutes.

To insure an adequate supply of developer, a spare spraycan 41 is also retained in the box 22, next to the operational can 42; should the latter run dry, a quick interchange of the cans, readily accessible after the lifting of top 38, as shown in FIGS. 3 and 4, restores the device to full service.

The pad 14 must also be replaced occasionally, the frequency depending primarily on the amount of use it receives and the relative humidity of the ambient atmosphere. This is readily accomplished by slipping the spent pad from its receptacle in top 38 and inserting a new pad in its place.

While many combinations of metallic salts and organic bases yield chelates suitable for use in the fingerprinting device 44, as stated earlier it has been found experimentally that ferric chloride and 8-hydroxyquinoline combine to form a particularly deep-colored and stable composition.

Ferric chloride is used in the anhydrous form and may be dispersed in glycerine, as will be described below in greater detail with reference to the manufacture of the pad 14.

The developer is preferably dissolved in acetone which is readily evaporated from the document surface and does not interact with it. The black chelate formed by this preferred combination of chemicals is particularly adapted to reproduction by any of the conventional photographic or xerographic processes. This latter feature is of importance since it permits copies of high quality to be made for use in performing the identification comparisons, and allows crisp images to be transmitted by telegraphic or electronic data link over considerable distances.

As disclosed above, the operation of the fingerprinting device 44 is greatly enhanced by the novel structure and characteristics of the pad 14. This pad is essentially a rigid slab of a composition including plaster of Paris, i.e., anhydrous calcium sulfate, which retains the liquid fingerprinting medium within its matrix and through capillary action provides a constant but limited supply of the medium at its upper surface. The pad is moist to the touch, but does not allow the liquid medium to pool, even when fully charged. This ensures that only those portions of the subject's skin in actual contact with the thin film of liquid on the pad surface receive the printing medium and, thereby effectively eliminates two of the greatest impediments to securing clear fingerprints with conventional inked pads, that is, the transfer or flowing of ink into the valleys between the ridges, and smudging.

The non-compressible pad is prepared by dissolving 1 gram of ferrous oxide in 200 cubic centimeters of water and adding 350 grams of plaster of Paris and 50 cubic centimeters of a finely divided, unpacked sawdust, preferably white pine. The above quantities may, of course, be increased or decreased as long as the proportions are substantially maintained. Variations of 10 or 15 percent by weight in these quantities will produce a usable, though less satisfactory pad.

The components are thoroughly intermixed and allowed to stand until the plaster begins to set. The process may be speeded up by continuous gentle stirring.

The viscous fluid is then charged into a mold of suitable shape. Such a mold 76 is shown in the perspective view of FIG. 5. The mold 76 is made of rubber and is rectangular in plan. Dimensions appropriate to a thumb-print pad would be of the order of 2 inches in length, 1½ inches in width, and ⅝ of a inch in depth.

Figure 5:
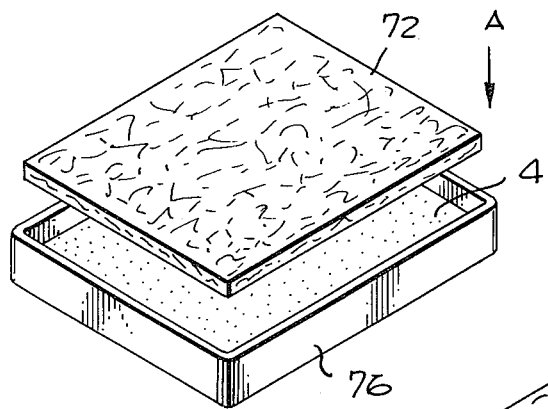
FIG. 5 is a perspective view of a mold for forming the hard-surfaced pad employed in the device of the invention, with a plaster-based slurry in place and a felt reinforcing layer about to be added.

The plaster-based composition 74 is added until the mold 76 is almost full, and a felt pad 72 is laid on top of it. The felt is cut somewhat smaller than the plane surface of the mold 76 and bonds to the wet plaster matrix. It serves the dual purpose of reinforcing the pad and acting as a reservoir for the fingerprinting medium. In FIG. 5 the felt pad 72 is shown being laid on the plaster, as indicated by the arrow A.

Figure 6:
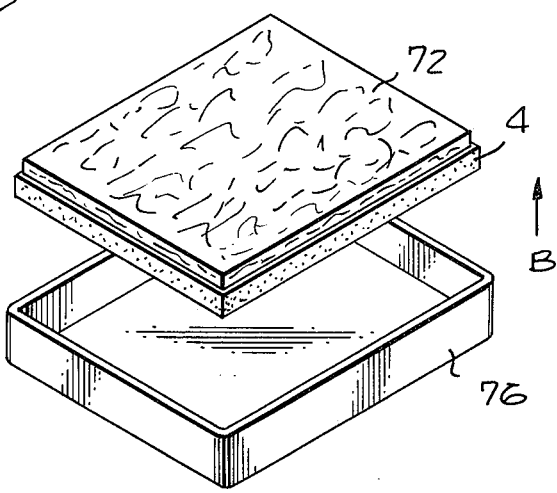
FIG. 6 is a perspective view of the mold of FIG. 5, with the composite pad being removed from the mold.

The composite pad is allowed to air dry for about 30 minutes and then removed from the mold 76, as shown in FIG. 6; the direction of relative motion being indicated by the arrow B.

In a final curing step the composite pad is exposed in a suitable oven to a temperature of about 160°F., for a period of about 1 hour. The dried pad is then allowed to cool.

The fingerprinting reagent is prepared by intermixing 50 grams of anhydrous ferric chloride ($Fe_2Cl_6$), 400 cubic centimeters of gylcerine and 50 cubic centimeters of water. To the homogeneous dispersion resulting from the above mixing process a small quantity, for example 0.05cc., of a conventional surfactant, such as the substance sold under the name "Liquinox" is added. Again, the proportions of these substituents may be varied within a range of 10 to 15 % by weight with acceptable results.

The composite pad is immersed in the reagent so prepared and allowed to soak for a long period, typically some 17 hours, to insure its saturation. The reagent permeates the porous plaster of Paris matrix and a substantial quantity is stored in the felt pad and in the sawdust dispersed through the matrix.

Figure 7:
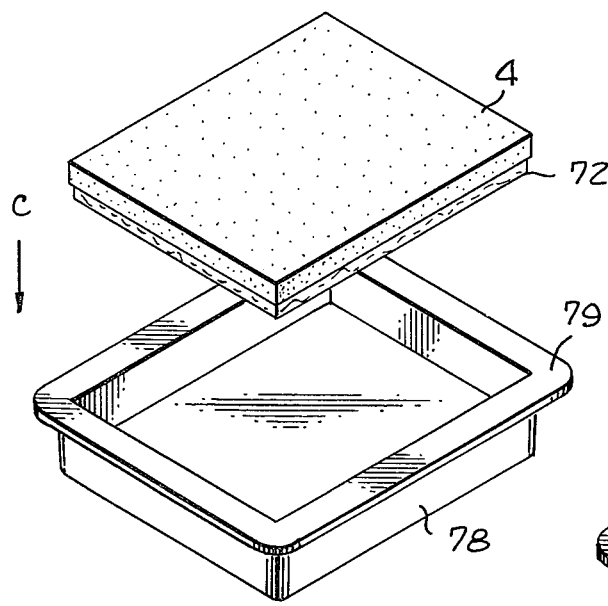
FIG. 7 is another perspective view, showing the completed pad in the process of assembly with its retaining pan.
Figure 8:
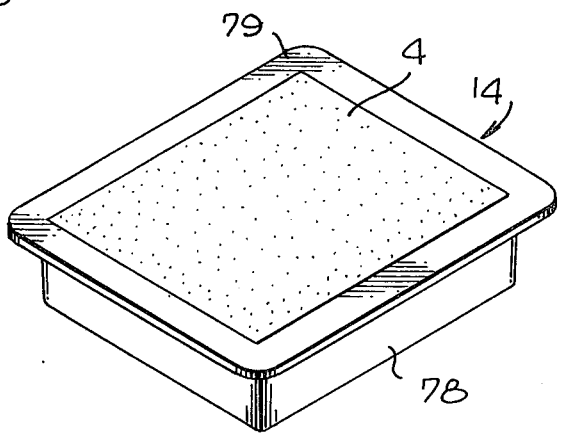
FIG. 8 is a view of the completed pad assembly, as employed in the fingerprinting device.

The saturated pad 14 is wiped off and pressed into a pan 78, so dimensioned that the pad is in tight frictional fit therein. The insertion step is shown in FIG. 7. The pad 14 is installed, by relative motion in direction of Arrow C, with the felt portion 72 nearest the bottom of the pan 78. The top surface of the plaster matrix 74 is substantially coplanar with a circumferential flange 79 of the pan. The flange 79 serves to retain the pad assembly 14 in the top 38 of the fingerprinting device.

Variations in the construction of the reagent carrying pad 14, in the exact composition of the chemicals employed in the reagent and in the developer used in conjunction therewith, and in the mechanical construction of the fingerprinting device are possible, and will become apparent to one skilled in the art upon exposure to the teachings herein. Such variations are considered to be within the scope of the invention as defined by the following claims.

What is claimed is:

1. The method of preparing a dispensing pad for fingerprinting reagents, comprising the steps of:
   preparing a plaster of Paris slurry;
   dispersing sawdust in said slurry;
   charging the slurry into a mold, and floating a layer of felt thereon;
   allowing the slurry to set in said mold;
   removing the hardened plaster matrix with the felt layer adhering thereto from said mold;
   drying said matrix at an elevated temperature for a predetermined period;
   preparing a reagent with metallic ions dispersed in a suitable solvent;
   submerging said plaster matrix with the felt layer adhering thereto in said reagent to saturate said matrix and said felt layer therewith; and
   inserting said pad into a fluid-tight pan with said plaster matrix exposed upwardly and said felt layer depending downwardly therefrom.

2. The method of claim 1, wherein said elevated temperature is less than the boiling point of water.

3. The method of claim 1, including adding a coloring agent to said slurry.

4. The method of claim 3, wherein said coloring agent is ferrous oxide.

5. The method of claim 1, wherein the volume of sawdust added to said plaster slurry is in a proportion of 1 part in 4.

6. The method of claim 5, wherein said temperature is about 160° F. and said predetermined period is 1 hour.

7. The method of claim 1, wherein said metallic ions are derived from a ferric salt and said solvent is glycerine.

8. The method of claim 7, wherein said ferric salt is ferric chloride.

9. The method of claim 1, wherein said mold has a planar, smooth base surface.

10. The method of claim 9, wherein said mold is substantially rectangular in plan.

* * * * *